United States Patent
Thalhammer et al.

(10) Patent No.: US 9,880,288 B2
(45) Date of Patent: Jan. 30, 2018

(54) SEMICONDUCTOR BIOSENSORS

(76) Inventors: Stefan Thalhammer, Munich (DE);
Markus Hofstetter, Hohenpolding (DE); John Howgate, Munich (DE); Martin Stutzmann, Erding (DE)

( * ) Notice: Subject to any disclaimer, the term of this patent is extended or adjusted under 35 U.S.C. 154(b) by 1181 days.

(21) Appl. No.: 13/377,551

(22) PCT Filed: Jun. 10, 2010

(86) PCT No.: PCT/EP2010/058183
§ 371 (c)(1),
(2), (4) Date: Mar. 22, 2012

(87) PCT Pub. No.: WO2010/142773
PCT Pub. Date: Dec. 16, 2010

(65) Prior Publication Data
US 2012/0171715 A1    Jul. 5, 2012

(30) Foreign Application Priority Data

Jun. 10, 2009 (EP) .................... 09007719
Jan. 20, 2010 (EP) .................... 10000550

(51) Int. Cl.
*G01N 33/487* (2006.01)
*G01T 1/02* (2006.01)

(52) U.S. Cl.
CPC ......... *G01T 1/02* (2013.01); *G01N 33/48728* (2013.01)

(58) Field of Classification Search
CPC .......... G01N 33/48707; H01L 21/8232; H01L 51/0512; H01L 29/772; H01L 2924/13064
See application file for complete search history.

(56) References Cited

U.S. PATENT DOCUMENTS

| | | | |
|---|---|---|---|
| 5,332,903 A | 7/1994 | Buehler et al. | |
| 6,340,568 B2* | 1/2002 | Hefti | 435/6.1 |
| 2006/0027756 A1* | 2/2006 | Thomson | G01T 1/026 250/370.07 |
| 2007/0046287 A1* | 3/2007 | Vervaeke et al. | 324/251 |
| 2007/0224128 A1* | 9/2007 | Dennis et al. | 424/10.1 |
| 2008/0069971 A1* | 3/2008 | Keersmaecker et al. | 427/555 |
| 2011/0132773 A1* | 6/2011 | Liemersdorf | G01N 27/4148 205/775 |

FOREIGN PATENT DOCUMENTS

| | | |
|---|---|---|
| DE | 198 40 157 | 6/2000 |
| FR | 2 775 694 | 9/1999 |
| WO | 00/05574 | 2/2000 |
| WO | WO 2009013101 A1 * | 1/2009 ......... G01N 27/4148 |

OTHER PUBLICATIONS

PCT Search Report for International Application No. PCT/EP2010/058183; dated Apr. 15, 2011.
Yu J., et al., (2007) *AlGaN/GaN heterostructures for non-invasive cell electrophysiological measurements*, Biosensors and Bioelectronics 23: 513-519.
Cimalla I., et al., (2007) *AlGaN/GaN biosensor—effect of device processing steps on the surface properties and biocompatibility*, Sensors and Actuators B 123: 740-748.
Lorenzelli L., et al., (2003) *Bioelectrochemical signal monitoring of in-vitro cultured cells by means of an automated microsystem based on solid state sensor-array*, Biosensors and Bioelectronics 18: 621-626.
Steinhoff G., et al., (2005) *Recording of cell action potentials with AlGaN/GaN field-effect transistors*, Applied Physics Letters 86: 033901-033901-3.
Poghossian A., et al., (2009) *Field-effect devices for detecting cellular signals*, Seminars in Cell & Developmental Biology 20: 41-48.
Morin, E.A., et al. (2016) *Facile Use of Cationic Hydrogel Particles for Surface Modification of Planar Substrates Toward Multifunctional Neural Permissive Surfaces: an in Vitro Investigation*; ACS Appl. Mater. Interfaces 8:5737-5745.

* cited by examiner

*Primary Examiner* — Paul S Hyun
(74) *Attorney, Agent, or Firm* — Kagan Binder, PLLC

(57) ABSTRACT

The present application relates to semiconductor devices, in particular to a device for monitoring a cell signal such as an electrical signal produced by living cells in response to external stimulation, optionally in real time, comprising (a) at least one discrete area comprising a high electron mobility transistor (HEMT); and (b) non-excitable cells attached to said HEMT (HEMT element) for example, fibroblasts, HEK, CHO cell lines, keratinocytes, etc. Preferably, the HEMT is an AlGaN/GaN FET. Accordingly, the device can be applied in uses and methods for monitoring a cell signal such as an electrical signal produced by living cells in response to external stimulation, optionally in real time. Likewise, the device can be applied for screening compounds that reverse, protect from and/or shield cells from external stimuli which cause damage to cells. Also, kits comprising the device are disclosed.

12 Claims, 9 Drawing Sheets

SEMICONDUCTOR BIOSENSORS

This application claims benefit from International Application No. PCT/EP2010/058183, which was filed on Jun. 10, 2010, which in turn claims priority to European Patent Application No. 09007719.9, filed on Jun. 10, 2009; and European Patent Application No. 10000550.3, filed on Jan. 20, 2010; wherein the entireties of said patent applications are incorporated herein by reference.

The present invention relates to semiconductor devices, in particular to a device for monitoring an cell signal such as an electrical signal produced by living cells in response to external stimulation, optionally in real time, comprising (a) at least one discrete area comprising a high electron mobility transistor (HEMT); and (b) non-excitable cells attached to said HEMT (HEMT element). Preferably, said device, and preferably said at least one discrete area which comprises a HEMT, has a surface suitable for cell attachment or growth. Accordingly, the device can be applied in uses and methods for monitoring an electrical signal produced by living cells in response to external stimulation, optionally in real time. Likewise, the device can be applied for screening compounds that reverse, protect from and/or shield cells from external stimuli which cause damage to cells. Also, kits comprising the device are an aspect of the present invention.

A transistor is an electrical device for switching, regulating and amplifying electrical currents or voltages. Transistors have three connections that are called source, drain and gate. The voltage applied at the gate-drain contacts determines the conductivity between the source and the drain. There are two main groups of transistors, the bipolar and the field effect transistors (FET's). The bipolar transistors change their space charge region at the pn-intersection depending on the applied current at the gate. Thus, the resistance between the source and the drain depends on the size of the space charge region. On the other hand the source-drain conductivity of a field effect transistor depends on the electrical field induced by the gate potential.

Figure 9:
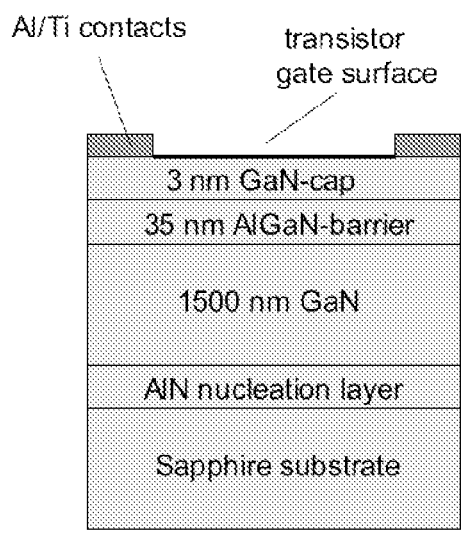

The first report of an ion sensitive field effect transistor (ISFET) was in 1972 (Bergveld P., 1972). Since then the understanding and improvement of ISFETs operating as pH sensors (van der Schoot B. H. et al., 1983; Steinhoff G. et al., 2003a) or detectors for biochemical processes in aqueous solutions (Matsuo T. and Wise K. D., 1974; Baumann W. H. et al., 1999) has been the subject of intense research. The measurement principle of an ISFET is similar to that of a normal FET. The source-drain conductivity depends on the space charge region, which is generated by a field effect. But instead of an electric contact for the gate there is an ion sensitive layer, for example $Al_2O_3$, $Si_3N_4$ or $Ta_2O_5$. A further improvement of this principle is the development of pH-sensitive High Electron Mobility Transistors (HEMT's). A schematic illustration is shown in FIG. 9. Instead of using a pH sensitive layer for ion detection they take advantage of the charge sensitivity of a two dimensional electron gas (2DEG) produced by the different polarisations of the materials (Dimitrov Roman, 2000).

The aim of radiation biology is to analyse the effects of i.e. ionising radiation on biological material. The main contribution comes from radioactivity ($\alpha$-, $\beta$- and $\gamma$-particles), x-rays and neutrons. In Germany the average exposure is 2.1 mSv/a due to natural radiation and about 1.8 mSv/a due to man-made radiation (Bundesamt für Strahlenschutz, 2007). Since different particles harm tissue in different ways one is using differing dose-weighting factors for the determination of the effective dose on tissue. This damage can be divided in two classifications: Deterministic radiation effects and stochastic radiation effects. Deterministic radiation effects occur after high doses and are immediately visible. They rise linear with the dose and have a threshold. On the other hand the stochastic radiation effects just occur with a certain probability after a specific dose. The difference between stochastic and deterministic effects can also be described on a microscopic level: As soon as a certain amount of cells are killed due to radiation and a visible effect is observable, one is talking about deterministic effects. Stochastic effects arise instead at doses where cell repair is possible. A dose of 1 Gy produces about 40 double strand breaks (DSB) (Whitaker S. J., 1992) and 1000 single strand breaks (SSB) (Ward J. F., 1988) in the DNA per cell. Thereof, double strand breaks are the most harmful damages due to the complexity of the repair mechanism. It depends on the number of DSB's if a cell starts to repair the DNA strand or the cell goes into apoptosis.

The dose response curve for stochastic effects is linear but it is not yet known if this is true for low doses since these effects are not directly visible. Stochastic effects are for example cancer, tumours or leukaemia. These diseases need a long time to develop and there is no possibility to determine exactly the origin of these diseases and especially how much influence comes from low radiation doses.

Therefore, new knowledge in understanding responses of cells to external stimulation is required. For example, it is desired to understand in radiation biology bystander effects, adaptive response, changes in gene expressions, genomic instability or cell abnormality. This understanding may lead to a reconsideration of the existing concept, that every radiation dose can be simply added to the overall radiation risk. A complex signalling system for information exchange on a cellular level is necessary to ensure cell homeostasis. Cell communication pathways lead to a transfer of primary and secondary messengers across the cellular membrane. Among other candidates for gap junction intercellular communication mediated primary bystander messenger are antioxidants, $Ca^{2+}$, Ip3 and cAMP, which is an important secondary messenger involved in the $Ca^{2+}$ metabolism. The decoding of cell communication systems is the key to understand the effects mentioned above.

There is a need in the art to provide systems which help to understand these effects. The present invention provides such systems.

The devices described herein below, whose discrete areas are preferably AlGaN/GaN-hetero-structures are capable of measuring cell potentials during irradiation experiments, for example in long-term measurements. By combining the GaN-chip measurement technique with, for example, irradiation experiments it will be possible to get new insights in radiation biology, for example signaling pathways, $Ca^{2+}$ burst measurements or bystander effect analysis. Cell analysis during radiation experiments is very difficult due to the exposure risk to X-rays for human beings. These are just a few examples of cell communication pathways but all these signalling systems might lead to a transfer of messengers across the cellular membrane. This transfer of charged particles fluxes is measurable with the developed measurement system of the present invention, which measurement system is based on heterostructures, preferably on GaN-transistors. The devices of the present invention provide the possibility to accomplish cell analysis in real time during, for example, radiation experiments from a distant place, which is not exposed to radiation.

The present work shows that the devices of the present invention (in particular the HEMT structures which are comprised by the discrete areas) are biocompatible and allow handling of living cells. It was shown that the behaviour of the cells is not affected by the devices described herein, in particular the chip surface itself. It was also shown that the devices of the present invention are sensitive enough to detect very small signals produced by living cells, for example before, during, and/or after an external stimulation such as radiation, as described herein.

Accordingly, in a first aspect, the present invention relates to a device for monitoring a cell signal, such as an electrical signal, produced by living cells in response to external stimulation, optionally in real time, comprising
(a) at least one discrete area comprising a high electron mobility transistor (HEMT); and
(b) non-excitable cells attached to said HEMT (HEMT element).

It is particularly preferred that said HEMT heterostructure is composed of group III nitrides. "Group III nitrides" are well known to the skilled person and include inter alia, Gallium nitride (GaN), Aluminum nitride (AlN), Indium nitride (InN) as well as mixed group III nitrides such as $Al_xGa_{l-x}N$ or $In_xGa_{l-x}N$ (0≤x<1), or $Al_xIn_yGa_{l-x-y}N$ (0>x>1, 0>y>1). A AlGaN/GaN-hetero-structure is particularly preferred.

It will be understood that a "device of the invention" sometimes also denoted as "device defined herein" etc. may be realized as a device comprising at least one discrete area comprising a high electron mobility transistor (HEMT), and (b) non-excitable cells attached to said HEMT (HEMT element). The devices of the present invention may optionally comprise at least one further discrete area comprising a high electron mobility transistor (HEMT), which further discrete area is free of cells. Said further discrete area may be used to isolate/adjust the measured cell signals for example by subtraction of the "blank value" which was measured in the mentioned further discrete area (optionally simultaneously). This device design as well as the corresponding analysis of the acquired data is explained in detail herein. The skilled person is of course aware of alternative measures which might also be used to isolate/adjust the cell signals (for example by way of subtraction of reference blank values which characterize a given HEMT). In certain embodiments, the present invention employs a device comprising at least one discrete area comprising a high electron mobility transistor (HEMT) wherein said are is free of cells.

The present invention further comprises embodiments, wherein the device comprises at least one discrete area comprising a high electron mobility transistor (HEMT) without cells attached to said HEMT. These "cell-free" devices are particularly suitable for measuring/determining/detecting/quantifying radiation does rates. This will be explained in more detail herein elsewhere. It is envisaged that the methods and uses disclosed herein may be carried out with the devices of the invention, i.e. with the devices having cells attached thereto (see above) or devices which are free of cells.

A "cell signal" as used herein denotes a measurable signal of the respective cell/test-cell in response to the external stimulus. "Measurable signal" thereby denotes a signal which can be monitored/quantified/detected/measured by the HEMT-elements which are comprised by the devices of the present invention. It will be understood that the HEMT-element comprised by the devices of the present invention "translates" all kinds of cell signals which are based on an alteration (increase or decrease) of the density and movement of charge carriers in the adjacency of the cells/test-cells into electrical signals, i.e. the device and in particular the HEMT element of the device of the present invention is able to monitor/quantify/detect/measure changes in the density of bound or unbound charge carriers, electrons and ions (for example $H^+$). A charge carrier denotes a free (mobile, unbound) particle carrying an electric charge. It follows that the monitored cell signals include alterations of the ion concentration, the electron concentration, the pH and/or of electrical signals of the cells, e.g. the movement of electrons, holes or ions etc.

Alterations of the pH and/or the ion concentration are preferred, pH-alterations being particularly preferred.

In a preferred aspect, said device, and preferably said at least one discrete area which comprises a HEMT, has a surface suitable for cell attachment or growth. A "surface suitable for cell attachment or growth" means that the surface is either used as such or, alternatively, that the surface is coated with a biological molecules or coatings which facilitate the attachment and/or growth of the cells. Examples of such coatings are well-known (for example from immunoassay techniques like ELISA etc. or from the BiaCORE system etc.) and include for example poly-Lysine, fibronectine, agarose etc.

In particular, the present invention demonstrates that the devices described herein, preferably AlGaN/GaN-heterostructures (in the following also named GaN-chips, chips or GaN-transistors), are capable of monitoring a cell signal such as an electrical signal produced by living cells in response to an external stimulation, for example, measuring cell potential responses, caused by, for example, charged extracellular messengers. This monitoring is possible before, during and/or after the external stimulation, preferably irradiation experiments in, preferably, long-term measurements.

The present invention shows the application of alternative material systems for the realisation of charge carrier sensitive field effect transistors such as AlGaN/GaN heterostructures, which can easily provide pH sensitive gate layers and can benefit from the high chemical stability of the group III-nitrides. At the interface of the two materials a fixed space charge appears due to the difference in polarisation of the two materials and a two-dimensional electron gas (2DEG) is produced. The electrical properties and therefore the conductivity of the system depend on the chip surface potential. In addition to this, the present invention shows that the transistor material itself does not influence living cells in any way. Due to this, for example, cell repair dynamics of DNA double strand breaks caused by X-rays are observed for cells grown on the GaN-surfaces.

In order to continually interpret the recorded data extensive characterisation of the transistors and the independently developed experimental set-up was performed which is described herein. The transistors show a stable and repeatable behaviour during irradiation experiments and are not damaged by, for example, X-ray radiation.

Furthermore, it is shown herein that the system is capable of measuring cell responses during irradiation experiments at low doses especially in the field of radiation biophysics and systems radiation biology. The sensitivity of the GaN-transistors is determined to −0.32 μA/pH. A monolayer of cells grown on the transistor gate excites a current change of 0.13 μA within 30 s at the transistor contacts during an irradiation with a dose rate of 7.1 mGy/s.

From the results described herein it can be concluded that the devices of the present invention enable specific investigations for cell responses and their chronological sequence. For example, by recording responses to external stimulation from neighbouring cells of, for example, irradiated cells, the possibility arises to conduct qualitative and quantitative experiments for possible bystander effects.

Devices of the invention and specific uses thereof are exemplified in great detail herein and particularly in the appended examples. These devices/uses can be generally applied in the context of the invention, i.e., the examples represent embodiments of the invention.

Preferably the devices of the invention are planar, and are flat or approximately flat. It is also preferred that the devices of the present invention are transparent, and can thus be subject to, for example, microscopic analysis.

The term "monitoring" when used in the context of the invention includes, but is not limited to, detecting, quantifying and/or measuring a cell signal such as an electrical signal.

The cell signal, such as an electrical signal, may be monitored in real time, i.e., during the external stimulation such as irradiation and/or after the external stimulation and/or before the external stimulation. It follows that the methods/uses of the present invention as well as the devices of the present invention may be used for real-time monitoring of a cell signal such as an electrical signal produced by living cells.

"External stimulation" includes physical or biophysical stimuli such as radiation, particle radiation, electric fields, magnetic fields, heat, light, nanoparticles, medicaments (drugs) and/or stimulation with a test compound. In the context of the present invention, it is also envisaged that more than one external stimulus is used simultaneously, i.e. at least two different sorts of stimuli are used at the same time, for example radiation and heat or radiation and test-compounds or test-compounds and heat etc. It is also envisaged to stimulate the cells in the presence of at least one substance which is capable or thought to be capable of preventing, reversing or enhancing the effect of the stimulus, thereby testing/screening the capability of such a substance to reverse or prevent or enhance the effect of the stimulus, for example of a test compound, drug, nucleic acid etc on the test cells, i.e. the non-excitable cells as defined herein.

A "test compound" is any compound whose activity or direct or indirect effect or effects on cells is investigated in any assay. A test compound can be any compound, including, but not limited to, drugs, medicaments, antibodies, siRNA, miRNA, aptamers, trinectines, antisense RNA, a nucleic acid, a small molecule, a large molecule, a molecular complex, an organic molecule, an inorganic molecule, a biomolecule or biological molecule such as but not limited to a lipid, a steroid, a carbohydrate, a fatty acid, an amino acid, a peptide, a protein, a nucleic acid, or any combination thereof. A test compound can be a synthetic compound, a naturally occurring compound, a derivative of a naturally-occurring compound, etc. The structure of a test compound can be known or unknown. In one application of the present invention, a compound is capable of, or is suspected of, effecting cell adhesion or cell spreading. In still another application, a compound is capable of, or is suspected of, interacting with cells (for example, binding to cell surface receptor, or inhibiting certain intracellular signal transduction pathway, or activating cells) In still another application, a compound is capable of, or is suspected of, affecting an ion channel activity (for example, blocking an ion channel).

Preferably, the mechanism of action of a test compound may be, for example, effects on cell viability, cell adhesion, apoptosis, cell differentiation, cell proliferation, cell morphology, cell cycle, IgE-mediated cell activation or stimulation, receptor-ligand binding, cell number, cell quality, cell spreading, or effects on ion channel activity (for example, an ion channel blocker), etc.

A living cell can respond in different ways. The response can, for example, be a change in the cell potential due to changed environmental influences, an initiation of cell repair mechanisms, a change in the cell cycle as well as an induction of apoptosis. All these reactions are responses to certain signalling pathways in the cell. All these responses can be monitored by way of the means and methods of the present invention.

Preferably, the focus of this work lies on monitoring cell responses before, during and/or after the irradiation with preferably ionising radiation at preferably low doses. "Low doses" includes a dose of radiation which does not kill the cells to be tested. The term "low dose" specifically includes radiation exposures at doses of 10 centigray (cGy) and below. The DOE Low Dose Radiation Research Program funds, for example, basic research to determine the responses induced by radiation exposures at doses of 10 centigray (cGy) and below, i.e. the term is well known in the art.

The test compound as described above may also be applied in the use of the device as defined herein for screening compounds that reverse, protect from and/or shield cells from external stimuli which cause damage to cells is an aspect of the present invention.

"Radiation" describes any process in which energy emitted by one entity travels through a medium or through space, ultimately to be absorbed by another entity. It also includes particle radiation, ionizing radiation (e.g., as occurring in nuclear weapons, nuclear reactors, and radioactive substances), but it can also refer to electromagnetic radiation (i.e., radio waves, infrared light, visible light, ultraviolet light, and X-rays) which can also be ionizing radiation, or to acoustic radiation. In the context of the invention, radiation is preferred and ionizing radiation is even more preferred.

Particle radiation is the radiation of energy by means of fast-moving subatomic particles. Particle radiation is referred to as a particle beam if the particles are all moving in the same direction, similar to a light beam.

In a particularly preferred embodiment of the devices/uses/methods of the present invention, it is envisaged that the external stimulation is radiation, and the cell signal to be monitored is an alteration of the pH.

All irradiation experiments in this work are performed with X-rays, which are electromagnetic waves with energies up to preferably 250 keV. X-rays are produced by a fast acceleration of charge carriers, called Bremsstrahlung, and an electron orbit transition in atoms or molecules, which is called the characteristic X-ray spectrum. Both effects occur in an X-ray tube. Accelerated electrons in an electric field are stopped rapidly by hitting an anode. The characteristic X-ray spectrum, which depends on the anode material, is overlaid with the spectrum of the Bremsstrahlung. X-rays interact with matter. The effects are called photoelectric effect, Compton effect and pair production. All these effects create secondary electrons and, thus, radiation with a different radiation quality. Therewith an exact dosimetry is very difficult. However, the present work and, in particular, the devices of the present invention overcome this difficulty, since they can be used for an exact dosimetry in that a response to an external stimulation, preferably irradiation on living cells can be monitored as described herein.

Preferably, all irradiated samples are covered with cell media, which provides a material for the mentioned effects to produce secondary electrons.

Non-excitable cells when used herein means cells which do not propagate and spread electrical signals such action potentials, i.e., which do not spontaneously generate an electrical signal, preferably an action potential.

"Non-excitable cells" include, for example, primary cells such as tumor cells, fibroblasts, keratinocytes, chondrocyte, sarcomas, carcinomas, endothelial cells, endodermal cells, liver stellate cells, mesothelioma cells, melanoma cells, trabecular-meshwork cells, cumulus cells, adipocytes, keratinocytes, epithelial cells, macrophages, cells of the immune system like lymphocytes; cell lines, preferably mammalian cell lines derived from human, horse, swine, goat, cattle, mouse or rat such as L-929, NIH 3T3 CHO, COS, HEK etc.

In a further embodiment said cell(s) is(are) comprised in a tissue.

"Primary cells" refers in this regard to cells which have been obtained from a subject, preferably, from a mammal, more preferably, a human, mouse or rat, particularly preferred from a human. Particularly preferred cells/test-cells are fibroblasts, L292 and/or, keratinocytes.

"Excitable cells" include at least cardiomyocytes, smooth muscle cells, pacemaker cells, Purkinje cells and nerve cells. These cells are specifically excluded from the present invention provided that they are the only sort/type of cells which is used in the context of the devices/uses/methods of the present invention.

It will be understood that in the context of the present invention, it is preferred to employ adherent cells, i.e., cells which are able to adhere to the devices of the invention.

The skilled person is well aware on how obtain/isolate/cultivate/propagate the cell(s) described herein.

In this regard, it is envisaged that the surface of the devices of the invention may be treated to allow/improve adherence of cells to said surface. Such treatments are well known to the skilled person and include, for example, coating of the devices with a biomolecular coating such as fibronectin, polylysine or cell glue. A "biomolecular coating" or a "biological molecule coating" is a coating on a surface that comprises a molecule that is a naturally occurring biological molecule or biochemical, or a biochemical derived from or based on one or more naturally occurring biomolecules or biochemicals. For example, a biological molecule coating can include an extracellular matrix component (e.g., fibronectin, collagens), or a derivative thereof, or can comprise a biochemical such as polylysine or poly-ornithine, which are polymeric molecules based on the naturally occurring biochemicals lysine and ornithine. Polymeric molecules based on naturally occurring biochemicals such as amino acids can use isomers or enantiomers of the naturally-occurring biochemicals.

An "extracellular matrix component" is a molecule that occurs in the extracellular matrix of an animal, such as a mammalian. It can be a component of an extracellular matrix from any species and from any tissue type. Nonlimiting examples of extracellular matrix components include laminins, collagens fibronectins, other glycoproteins, peptides, glycosaminoglycans, proteoglycans, etc. Extracellular matrix components can also include growth factors.

A biomolecular coating may also include a natural ligand or an agonist or an antagonist for a cell surface receptor of the respective cell (for example, antibodies coated on the devices of the invention which bind to the cells of the invention and thereby attach them to the surface of the devices).

Thanks to the present invention it is now possible to monitor the individualized cellular response of a subject (for example, tumor cells obtained from a tumor patient or fibroblasts obtained from a subject) by way of obtaining such cells from such subjects, attaching said cells to the HEMT as defined herein and monitoring the cellular response (for example the response to an external stimulus like an anti-tumor agent such as an antibody etc.).

Accordingly, the present invention also relates to a device for monitoring a cellular response, optionally in real time comprising (a) a high electron mobility transistor (HEMT); and (b) non-excitable cells attached to said HEMT, wherein said non-excitable cells have been obtained from a subject.

HEMT stands for High Electron Mobility Transistor, and is also known as heterostructure FET (HFET) or modulation-doped FET (MODFET). A HEMT is a field effect transistor incorporating a junction between two materials with different band gaps (i.e., a heterojunction) as the channel instead of a doped region. It is envisaged that the mentioned materials comprises group III-nitrides which are normally used in material combinations. A commonly used material combination is GaAs with AlGaAs, though there is wide variation, dependent on the application of the device. Devices incorporating more indium generally show better high-frequency performance, while in recent years, gallium nitride HEMTs have seen a massive increase in research effort, due to their high-power performance. In the context of the present invention HEMTs which are composed of GaN/AlGaN/heterostructures are preferred.

It is also envisaged that the HEMTs described herein are realized as an ISFET. An "ISFET" is an ion-sensitive field-effect transistor used to measure ion concentrations in solution; when the ion concentration (such as pH) changes, the current through the transistor will change accordingly.

The combination of multiple heterojunctions together in a device is called a "heterostructure" although the two terms are commonly used interchangeably. A heterojunction is the interface that occurs between two layers or regions of dissimilar crystalline semiconductors. These semiconducting materials have unequal band gaps as opposed to a homojunction.

In general, to allow conduction, semiconductors need to be doped with impurities to generate mobile electrons in the layer. However, this causes electrons to slow down because they end up colliding with the impurities which were used to generate them in the first place. HEMT, however, is a smart device to resolve this seemingly inherent unsolvable contradiction.

HEMT accomplishes this by use of high mobility electrons generated using the heterojunction of a highly-doped wide-bandgap n-type donor-supply layer and a non-doped narrow-bandgap channel layer with no dopant impurities. For example, the electrons generated in a n-type AlGaAs thin layer drop completely into the GaAs layer to form a depleted AlGaAs layer, because the heterojunction created by different band-gap materials forms a quantum well (a steep canyon) in the conduction band on a GaAs side where the electrons can move quickly without colliding with any impurities because the GaAs layer is undoped, and from which they cannot escape. The effect of this is to create a very thin layer of highly mobile conducting electrons with very high concentration, giving the channel very low resistivity (or to put it another way, "high electron mobility"). This layer is called a two-dimensional electron gas. As with all the other types of FETs, a voltage applied to the gate alters the conductivity of this layer.

Ordinarily, the two different materials used for a heterojunction must have the same lattice constant (spacing between the atoms). As an analogy, imagine pushing together two plastic combs with a slightly different spacing.

At regular intervals, you'll see two teeth clump together. In semiconductors, these discontinuities are a kind of "trap", and greatly reduce device performance.

As used herein, "said device has a surface suitable for cell attachment or growth" means that the device, preferably the HEMT element has chemical or biological properties such that cells of interest can viably attach on the surface and new cells can continue to attach, while the cell culture grows, on the surface. However, it is not necessary that the device, preferably the HEMT element, contains substances necessary for cell viability or growth. These necessary substances, e.g., nutrients or growth factors, can be supplied in a medium. For example, when a suspension of cells applied in the context of the invention such as viable, unimpaired, epithelial or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

It is preferred that the cells are confluent on the device of the invention, in particular on the HEMT element. It is also preferred that the cells grow as a monolayer, however multilayer growth of the cells is also envisaged. Preferably, only a (one) cell "type" is grown on the HEMT element of the devices of the invention (e.g. fibroblasts). It is, however, also envisaged that more than one cell type is grown on the HEMT element of the devices of the present invention, i.e. one device, particularly the HEMT element thereof, may comprise two, three, four, five, six etc. different cell types (for example a primary cell and the corresponding immortalized tumor cell). These different cell types may be located on one and the same and/or on discrete HEMT elements which are located on the devices of the present invention.

It will be understood that the devices of the present invention may comprise more than one discrete area comprising a HEMT element, i.e. devices are envisaged that comprise two, three, four, five, ten, fifteen, twenty, 30, 40, 50, 60, 70, 80, 90, 100 or even more discrete HEMT elements each comprised by a discrete area. It is envisaged that some of these discrete areas comprising a HEMT element comprise reference substances (for example merely the biomolecular coating(s); and/or cells of different origin in respect of the "test cell", i.e. the test cell whose a cell signal such as an electrical signal in response to external stimulation is monitored; and/or non-living test cells; etc.) which reference substances will aid to calibrate the system. It is also envisaged that the device of the present invention comprises at least two discrete HEMT elements both of which comprise the same type of non-excitable cells as defined herein, wherein the cells at these at least two discrete HEMT-elements are stimulated by different external stimuli. "Different external stimuli" includes that the distinct HEMT elements are stimulated by the same sort of stimulus (for example radiation) which is applied in different intensity, different exposure and/or by different sorts of stimuli (for example radiation and heat).

Alternatively or additionally, it is also envisaged that at least one of at least two discrete HEMT elements on the devices of the present invention is free of cells and also free of biomolecular coatings. Such a device is preferred.

It is envisaged that the discrete areas mentioned herein are in a size of about 1, 2, 3, 4, 5, 6, 7, 8, 9, 10 or even more square millimeter(s), about five square millimeters or less being preferred and about one square millimeter being particularly preferred.

The GaN-chips used for the experiments in this work consist of different layers of semiconductor materials in the nanometer scale. The composition profile of these structures is important since it determines the local band structure of the chip device. One of the most important properties of the hexagonal group-III nitrides is the extensive spontaneous and piezoelectric polarisation compared to other materials (Dimitrov R., 2000). Different material properties and polarisations of the hetero-structures force the charge carriers to accumulate at the interface region without any additional doping. This leads to an electrostatic potential.

Further, the use of at least one discrete area comprising a HEMT for the manufacture of a device for monitoring a cell signal such as an electrical signal produced by living cells in response to external stimulation, optionally in real time is an aspect of the present invention.

The use of at least one discrete area comprising a HEMT for the manufacture of a device for monitoring/quantifying/detecting/measuring of radiation and/or alterations in the density of bound or unbound charge carriers (alterations of the pH and/or the ion-concentration being preferred, pH-alterations being more preferred), optionally in real time, is also an aspect of the present invention.

Furthermore, the use of the device as defined herein for monitoring a cell signal such as an electrical signal produced by living cells in response to external stimulation is an aspect of the present invention.

Moreover, the use of the device as defined herein for screening compounds that reverse, protect from and/or shield cells from an external stimulus which causes damage to cells is an aspect of the present invention.

An "external stimulus" can be a physical, biophysical, chemical or biological stimulus such as for example radiation, particle radiation, heat, light, nanoparticles, medicaments (drugs) and/or stimulation with a test compound.

Also, a kit comprising the device as defined herein is an object of the present invention.

In a further aspect, the present invention relates to a kit comprising the at least one discrete area comprising a HEMT as defined herein and at least one of the following items:
(a) means and/or instructions to attach non-excitable cells attached to said HEMT;
(b) means and/or instructions to grow non-excitable cells;
(c) non-excitable cells;
(d) means and/or instructions to isolate non-excitable primary cells; and/or
(e) means and/or instructions for monitoring a cell signal such as an electrical signal produced by living non-excitable cells in response to external stimulation.

In another aspect, the present invention relates to a method for monitoring a cell signal such as an electrical signal produced by living cells in response to external stimulation, comprising:
(a) providing a device as defined above; and
(b) monitoring a cell signal such as an electrical signal produced by living cells in response to external stimulation.

Further, the present invention relates to a (preferably in vitro) method for monitoring a cell signal such as an electrical signal produced by living cells in response to external stimulation, comprising:
(a) providing at least one discrete area comprising a HEMT;
(b) growing/attaching non-excitable cells on said discrete area; and
(c) monitoring a cell signal such as an electrical signal produced by living cells in response to external stimulation.

The devices of the present invention may be used in accordance with any of the following items:
(1) Use of the device as defined herein above for monitoring/measuring the influence of external stimuli on cell growth, cell adhesion and cell morphology.
(2) Use of the device as defined herein for monitoring/measuring cell growth, cell adhesion and cell morphology without external stimuli.
(3) Use of the device as defined herein for recording cell-cell communication parameters/pathways.
(4) Use of the device as defined herein for measuring/detecting/quantifying radiation dose rates. The term "radiation dose rate" is well known and means "radiation dose (dosage) absorbed per unit of time".

We present the real-time X-ray irradiation response of charge and pH sensitive solution gate AlGaN/GaN high electron mobility transistors (HEMTs). At the interface of the two materials a fixed space charge appears due to the difference in polarisation of the materials and a two-dimensional electron gas (2DEG) is produced. The electrical properties and therefore the conductivity of the system highly depend on the chip surface potential. We could demonstrate that the devices are stable and show reproducible behavior under and following X-ray radiation at different energies, including a linear integrated response with dose into the micro-gray range. Titration measurements of devices in solution reveal that the linear pH response and sensitivity are not only retained under X-ray irradiation, but an irradiation response could also be measured. The active areas of the sensors are in the size of about 1 mm$^2$, which makes them an ideal candidate for dose determination in radiology applications. The devices are bio-compatible and can be simultaneously operated in aggressive fluids and under hard radiation. The development of this sensor device, which provides the possibility of online radiation dosimetry acquisition during biosensing applications, has a huge potential in radiation biophysics.

Thus the present invention discloses for the first time that a device comprising at least one HEMT (which is free of cells, i.e. comprises no cells attached thereto) is able to measure/detect/quantify radiation. This effect is shown in the appended examples, which demonstrate that the devices described herein are well-suited for dosimetry purposes and even provide an internal calibration for the absolute received dose-rate under solution operation. It is thus envisaged that the devices described herein and in particular devices which are characterized by a discrete area comprising a HEMT in a "cell-free" setting meaning the HEMT heterostructure is used as such, i.e. is free of cells (but also devices whose discrete areas comprise cells, preferably non-excitable cells, attached to the area comprising a HEMT) are used for the measurement/detection/quantification of radiation or radiation dosimetry. Said measurement/detection/quantification may take place in solution (including in vivo and in vitro settings) or in air (for illustration see the appended Examples). Additionally, the devices work for very high cumulative doses and show no permanent effects after irradiations of several 100 Gy. The devices are tested for dose rates from about 1 µGy/s to 10 mGy/s (high dose).

HEMT-based devices of the present invention, preferably those which comprise a AlGaN/GaN heterostructure, reach their detection limit in the µGy-regime while the known MOSFET-based radiation detectors already reach their detection limit in the low mGy region. The devices comprising a HEMT which form part of the present invention, preferably those which comprise a AlGaN/GaN heterostructure, provide therefore an unexpected but superior alternative to the MOSFET-based radiation dosimeters which were already at hand. (see the appended examples).

"µGy-regime" includes doses of up to 1000 µGy and below, preferably about 900, 800, 700, 600, 500, 400, 300, 200, 100 µGy or below, more preferably about 90, 80, 70, 60, 50, 40, 30, 20, 10 µGy or even lower doses of about 10, 9, 8, 7, 6, 5, 4, 3, 2, 1 µGy or even below, such as does of about 0.9, 0.8, 0.7, 0.6, 0.5, 0.4, 0.3, 0.2, 0.1 µGy or even below.

(5) Use of the device as defined herein for radiation dosimetry. "Radiation dosimetry" is the calculation of the absorbed dose in matter and tissue resulting from the exposure to indirectly and directly ionizing radiation. The devices described herein (preferably HEMT-based devices, more preferably those which comprise a AlGaN/GaN heterostructure) may also be used for entrance surface dose measurements, for example on (or in) human patients, preferably in real-time.
(6) Use of the device as defined herein for performing combined surface potential and radiation dosimetry, optionally in real-time. As it was shown for the first time by the present invention, HEMT devices retain their sensitivity to potential changes at the surface (preferably the AlGaN/GaN surface) during irradiation in solution. Thus, it is possible to use the devices comprising a HEMT of the present invention, preferably those which comprise a AlGaN/GaN heterostructure, for the simultaneous or time-delayed measurement of the pH and radiation. It is also envisaged to use the devices comprising a HEMT of the present invention, preferably those which comprise a AlGaN/GaN heterostructure, for the simultaneous or time-delayed measurement of a cell signal and radiation.
(7) Use of the device as defined herein for screening test-compounds which exert a desired effect on the (test) cells. "desired effect" thereby depends on the intention of the experiment, i.e. it might be desired to screen for compounds which exert a beneficial or detrimental (for example toxic) effect on a cell, or which exert an anti-proliferative effect on tumor cell; or compounds which exert an proliferative effect on cell; or compounds which reverse or enhance the detrimental effect of the external stimulus (for example that of ionizing radiation); or compounds which trigger (e.g. in an agonistic or antagonistic way) a certain biochemical pathway in a cell (for example a pathway which is involved in a pathogenic setting); or a compound which may act as a drug in a medical setting. "A compound" thereby also includes a plurality of test-compounds. "Test-compounds" has been defined herein elsewhere.
(8) Use of the device as defined herein for screening the effective concentration of a test-compounds which concentration is necessary to exert a desired effect on the (test) cells. "Effective concentration" thereby means the concentration of the test compound which is needed in order to exert the desired effect. Desired effect has been defined herein above.

The present invention also relates to the devices defined herein for use in the above settings and in particular to the measurement/quantification/detection of radiation and/or alterations in the density of bound or unbound charge carriers (alterations of the pH and/or the ion-concentration being preferred, pH-alterations being more preferred). The alteration mentioned hereinbefore may result from a cell signal (said cell being attached to at least one HEMT) or may result from alterations in solution or both.

"In solution" includes in vitro and in vivo settings, i.e. it is envisaged to employ the devices described herein ex vivo (e.g. as a dosimeter which is taken along) or in vivo e.g. an implantable device which measures/detects/quantifies alterations of bound or unbound charge carriers (alterations of the pH and/or the ion-concentration being preferred, pH-alterations being more preferred) and/or radiation (simultaneously or time-delayed).

It is envisaged that the above mentioned measurements/uses are carried out in real time or time delayed.

It is further envisaged that the devices of the present invention are medical devices.

It will be understood that the use of the devices of the invention for screening purposes may be carried out in any suitable setting, like for example in a high-throughput setting, or a setting suitable for a high-content screening (i.e. a screening system wherein several different parameters are monitored simultaneously). The skilled person is well aware on how to adapt the devices of the present invention to such a setting.

Further aspects and embodiments of the present invention are derivable from the following sections.

The present work has shown that the devices described herein, preferably AlGaN/GaN-heterostructures, are capable of monitoring a cell signal such as electrical signal produced by living cells in response to external stimulation, for example, it is shown that the devices can be used for measuring cell membrane potentials, preferably in the field of radiation biology and/or radiation research in general. The possibility of measuring cell potentials, not only after irradiation experiments but also during the irradiation itself expands the examination restrictions in an enormous way. This examination method opens a huge field of new experiments. Thanks to the present invention, it is possible to monitor reactions of cells in response to external stimulation from the first moment of the external stimulus which is preferably irradiation. This enables specific investigations for cell responses and their chronological sequence.

In addition to monitor a cell signal such as an electrical signal produced by living cells, preferably single cells on the chips in response to external stimulation, it is envisaged to set up a single cell stimulation, for example a single cell irradiation. For this purpose a micro-beam, which has a beam diameter less than a single cell, is used. This can be accomplished at the SNAKE (superconducting nanoprobe for applied nuclear physics experiments) set-up at, for example, the Munich Tandem Accelerator.

It is furthermore envisaged that a chip holder is developed which provides the possibility of connecting measurement cables. The aim of this construction is to measure cell potentials during micro beam irradiation. By recording responses from neighbour cells of the irradiated cells, the possibility arises to do qualitative and quantitative experiments for a possible bystander effect (Belyakov O. V. et al., 2002; Prise K. M. et al., 2003; Prise K. M. et al., 2002; Belyakov O. V. et al., 2005; Larimore S. A. et al., 2003). This is an embodiment of the invention which can be applied in connection with the uses, methods and kits described herein.

It is also envisaged that the devices of the present invention may be implanted so as to allow in vivo monitoring a cell signal such as an electrical signal produced by living cells in response to external stimulation, preferably radiation, particularly preferred irradiation.

Preferred Layout of the Nano-Structures

The following passage illustrates preferred layouts of the heterostructures of the present invention, although it must be understood that the present invention is not limited to these settings. The GaN-chips have electrical contacts and are used for cell potential measurements. A sapphire substrate is covered with an AlN nucleation layer. The area of operations consists of a 2500 nm GaN layer and a 25 nm AlGaN barrier with an aluminium content of 28%. The two-dimensional electron gas carrier density between these two materials is $6.1 \cdot 10^{12}$ cm$^{-2}$ (Steinhoff G. et al., 2003b). The device is covered with a 3 nm GaN cap layer, which is the surface where the cells are cultivated.

Illustrated Handling of the Nano-Structures

The following passage illustrates preferred settings of the heterostructures of the present invention, although it must be understood that the present invention is not limited to these settings. The chips were cleaned with acetone and isopropanol in an ultrasound bath before wiring and passivation. Before every single measurement they were cleaned with 70% ethanol, just as the GaN-samples. There was one GaN-sample available with a polished backside. All the other used GaN-samples and chips do not have a polished backside. With these samples light optical microscopy was not possible.

Illustration of a Possible Measurement Set-up and Data Acquisition

The following passage illustrates preferred settings of the present invention, although it must be understood that the present invention is not limited to these settings. The GaN-chips are mounted on a sample holder and are connected with gold wires, which have a diameter of 0.1 mm. Data acquisition is accomplished with Keithley Source- and Multimeters (Keithley Instruments Inc., Cleveland, Ohio 44139). Every GaN-chip is connected to a Keithley 2400 Source-meter, which provides the possibility to apply a voltage and measure current simultaneously. The SourceMeter combines a precise, low-noise, highly stable DC power supply with a low-noise, highly repeatable, high-impedance multimeter. It has 0.012% basic accuracy with 5½-digit resolution. At 5½ digits, the SourceMeter delivers 520 readings/second over the IEEE-488 bus (Model 2400 Series SourceMeter User's Manual, Revision G, 1998, Keithley Instruments, Inc.) A constant voltage of 120 mV was applied to the source-drain contacts of the GaN-transistors while measuring simultaneously the current. The given accuracies are valid for basic settings of the devices. With different integration times for the readings the accuracies can differ from the given values. The Keithley devices send their data to a GBIP Interface Board, type KPCI-488LP IEEE-488.2 (Keithley Instruments Inc., Cleveland, Ohio 44139), which is installed in a Windows XP based PC. Control and read out of the measurement devices as well as storage of the sampled data is done with LabView 8.6.1 Express (National Instruments Dtl., München, Germany). For all irradiation experiments a medical X-ray machine, type Stabilipan TR300f (Siemens AG, München, Germany), was used.

Characterisation of the GaN-Transistors

Before starting with cell potential measurements it is envisaged to evaluate the dependence of the transistor device on different physical environment influences. The GaN-chips are very sensitive to light, temperature and pH-value changes and show responses to X-ray radiation. In order to make a reasonable interpretation of the measured data, an extensive characterisation of the transistors is advisable for getting acquainted with the physical and electrical properties. Preferably, an individual characterisation of every single chip (heterostructure or device of the invention) is carried out.

pH Sensitivity of the Devices of the Present Invention

There are several publications describing a pH-value change when a cell undergoes apoptosis (Lagadic-Gossmann D. et al., 2004; Tannock I. F., 1989). To get a feeling of the expected signal changes during cell irradiation experiments, the GaN-transistor current is measured in dependency of the pH-value. For this purpose, solutions with different pH-values were produced by mixing HCl and NaOH. The pH-value of the solutions was determined with a pH-meter, type CyberScan 500 (Eutech Instruments Europe, Nijkerk, Netherlands).

Biocompatibility and Cell Vitality

Extensive cell growth experiments were performed to ensure that the cells on the GaN-surface are vital and that there are no cellular effects from the substrate materials. The morphological examinations and growth studies were carried out either by light optical microscope or laser scanning microscope and atomic force microscope (AFM). One of the easiest ways to determine if a cell is alive or dead is to examine its outer shape. Cell growth on the GaN-chips was compared to cell growth on ordinary microscope slides. It was observable that there is no visible difference between cell growth on GaN-surfaces and glass substrates.

REFERENCES

Alberts Bruce, Johnson Alexander, Lewis Julian, Raff Martin, Roberts Keith, Walter Peter
*Molecular Biology of the Cell*, 4$^{th}$ edition (2002)

Baumann W. H., Lehmann M., Schwinde A., Ehret R., Brischwein M., Wolf B.
*Microelectronic sensor system for microphysiological application on living cells*. Sensors and Actuators B 55 (1999)

Baur B., Howgate J., von Ribbeck H.-G., Gawlina Y., Bandalo V., Steinhoff G., Stutzmann M., Eickhoff M.
*Catalytic activity of enzymes immobilized of AlGaN/GaN solution gate field-effect transistors*. Applied Physics Letters 89, 183901 (2006)

Belyakov Oleg V., Mitchell Stephen A., Parikh Deep, Randers-Pehrson Gerhard, Marino Stephen A., Amundson Sally A., Geard Charles R., Brenner David J.
*Biological effects in unirradiated human tissue induced by radiation damage up to 1 mm away*. PNAS, Vol. 102, No. 40 (2005)

Belyakov O. V., Folkard M., Mothersill C., Prise K. M., Michael B. D.
*Bystander-induced apoptosis and premature differentiation in primary urothelial explants after charged particle microbeam irradiation*. Radiation Protection Dosimetry Vol. 99, Nos 1-4 (2002)

Bergveld P.
*Development, Operation, and Application of the Ion-Sensitive Field-Effect Transistor as a Tool for Electrophysiology*. Biomedical Engineering, IEEE Transactions on Volume BME-19, Issue 5 (September 1972)

Bernardini Fabio, Fiorentini Vincenzo
*Spontaneous polarization and piezoelectric constants of III-V nitrides*. Phys. Rev. B 56, R10024-R10027 (1997)

Bernardini Fabio, Fiorentini Vincenzo
*Nonlinear macroscopic polarization in III-V nitride alloys*. Phys. Rev. B 64, 085207 (2001)

Berridge Michael J., Irvine Robin F.
*Inositol phosphates and cell signalling*. Nature 341 (21 Sep. 1989)

Critchlow Susan E., Jackson Stephen P.
*DNA end-joining: from yeast to man*. Trends in Biochemical Sciences, Volume 23, Issue 10 (1998)

Dimitrov Roman
*Herstellung and Charakterisierung von AlGaN/GaN-Transistoren*. Selected Topics of Semiconductor Physics and Technology, Vol. 28 (2000)

Green L. M., Murray D. K., Tran D. T., Bant A. M., Kazarians G., Moyers M. F., Nelson G. A.
*Response of Thyroid Follicular Cells to Gamma Irradiation Compared to Proton Irradiation. I. Initial Characterization of DNA Damage, Micronucleus Formation, Apoptosis, Cell Survival, and Cell Cycle Phase Redistribution*. BioOne Volume 155, Issue 1 (2001)

Hofstein S. R., Heiman F. P.
*The silicon insulated-gate field-effect transistor*. Proceedings of the IEEE Volume 51, Issue 9 (September 1963)

Lagadic-Gossmann D., Huc L., Lecureur V.
*Alterations of intracellular pH homeostasis in apoptosis: origins and roles*. Cell Death and Differentiation 11 (2004)

Larimore S. A., Wright E. G.
*Radiation-induced genomic instability and bystander effects: related inflammatory-type responses to radiation-induced stress and injury?* A review. Int. J. Radiat. Biol. Vol. 79, No. 1 (2003)

Link Angela
*Zweidimensionale Elektronen-and Löchergase in GaN/AlGaN Heterostrukturen*. Selected Topics of Semiconductor Physics and Technology, Vol. 66 (2004)

Matsuo Tadayuki, Wise Kensall D.
*An Integrated Field-Effect Electrode for Biopotential Recording*. Biomedical Engineering, IEEE Transactions on Volume BME-21, Issue: 6 (1974)

Prise Kevin M., Folkard Melvyn, Michael Barry D.
*Bystander responses induced by low LET radiation*. Oncogene 22 (2003)

Prise K. M., Belyakov O. V., Newman H. C., Patel S., Schettino G., Folkard M., Michael B. D.
*Non-targeted effects of radiation: Bystander responses in cell and tissue models*. Radiation Protection Dosimetry Vol. 99, Nos 1-4 (2002)

Rothkamm Kai, Löbrich Markus
*Evidence for a lack of DNA double-strand break repair in human cells exposed to very low x-ray doses*. PNAS, Vol. 100, No. 9 (2003)

Saez J. C., Connor J. A., Spray D. C., Bannet M. V.
*Hepatocyte gap junctions are permeable to the second messenger, inositol 1,4,5-triphosphate, and to calcium ions*. Proc Natl Acad Sci USA, 86(8), (1989)

Steinhoff Georg, Purrucker Oliver, Tanaka Motomu, Stutzmann Martin, Eickhoff Martin $Al_xGa_{1-x}N$—*A new Material System for Biosensors*. Adv. Funct. Matter., 13, No. 11 (2003)

Steinhoff G., Hermann M., Schaff W. J., Eastman L. F., Stutzmann M., Eickhoff M.
*pH response of GaN surfaces and ist application for pH-sensitive field-effect transistors*. Applied Physics Letters, Volume 83, Number 1 (2003)

Steinhoff Georg, Baur Barbara, Wrobel Günter, Ingebrandt Sven, Offenhäusser Andreas, Dadgar Armin, Krost Alois, Stutzmann Martin, Eickhoff Martin
*Recording of cell action potentials with AlGaN/GaN field-effect transistors*. Applied Physics Letters 86, 033901 (2005)

Tannock Ian F., Rotin Daniela
*Acid pH in Tumors and Its Potential for Therapeutic Exploitation*. Cancer Research 49 (Aug. 15, 1989)

Tsubouchi K., Sugai K., Mikoshiba N.
*AlN Material Constants Evaluation and SAW Properties on AlN/Al2O3 and AlN/Si*. IEEE Ultrasonics Symposium 90, 375 (1981)

van der Schott B. H., Bergveld P., Bos M., Bousse L. J.
*The ISFET in Analytical Chemistry*. Sensors and Actuators, 4 (1983)

Ward J. F.
*DNA damage produced by ionizing radiation in mammalian cells: identities, mechanisms of formation, and reparability*. Prog. Nucl. Acid Res. Mol. Biol. 35 (1988)

Whitaker S. J.
*DNA damage by drugs and radiation: what is important and how is it measured?* Eur. J. Cancer 28 (1992)

Wright A. F.
*Elastic properties of zinc-blende and wurtzite AlN, GaN, and InN*. J. Appl. Phys. 82, 2833 (1997)

Zoroddu Agostino, Bernardini Fabio, Ruggerone Paolo
*First-principles prediction of structure, energetics, formation enthalpy, elastic constants, polarization, and piezoelectric constants of AlN, GaN, and InN: Comparison of local and gradient-corrected density-functional theory*. Phys. Rev. B 64, 045208 (2001)

This disclosure may best be understood in conjunction with the accompanying drawings, incorporated herein by references. Furthermore, a better understanding of the present invention and of its many advantages will be had from the following examples, given by way of illustration and are not intended as limiting.

Figure 1:
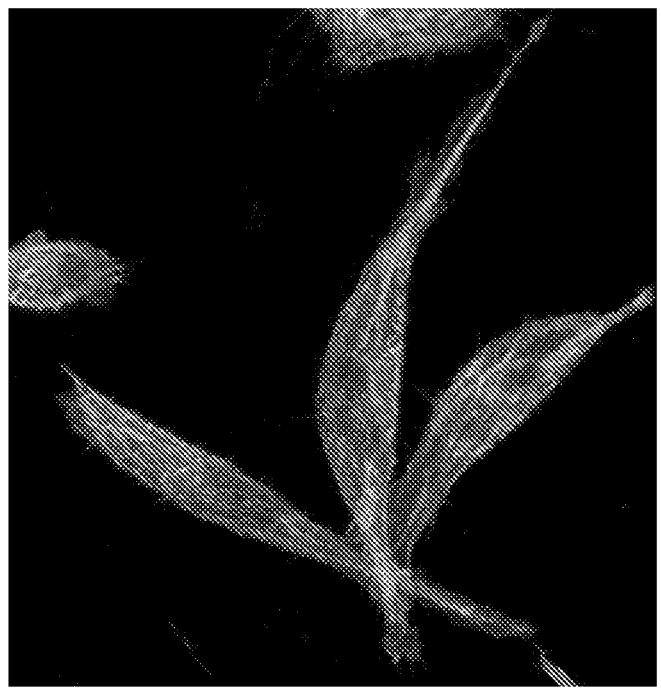

The Figures Show:

FIG. 1: Laser scanning confocal microscopic image of fibroblasts grown on a GaN-surface. The cell membrane is labeled with DiO, the F-Actin with Rhodamine-Phalloidin and the cell nuclei with Hoechst 33342. (Scale bar: 40 μm)

Figure 2:
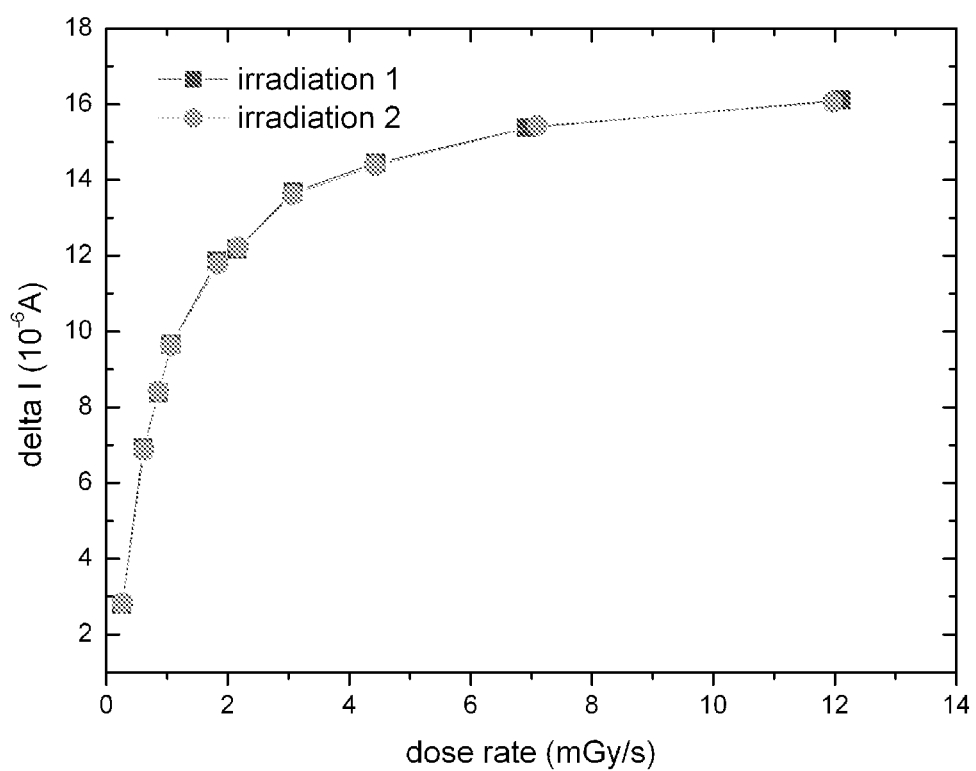

FIG. 2: Transistor response on different dose rates: ΔI is the change of the transistor source-drain current caused by two different, nominally identical X-ray radiations.

Figure 3:
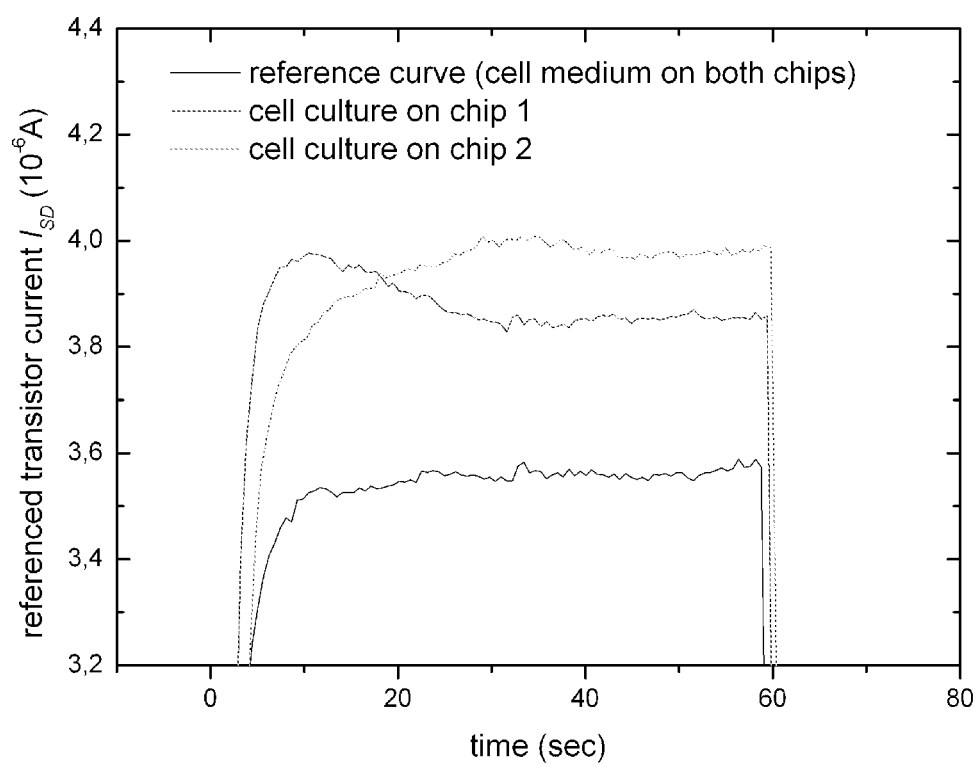

FIG. 3: Cell irradiation experiment (7.1 mGy/s, 60 s). The three curves show current difference calculations of two simultaneous irradiated GaN-transistors. The black curve represents the reference; on both chips only cell medium. The red line was recorded with cells grown on one of the GaN-chips and the green line with interchanged measurement and reference chip.

Figure 4:
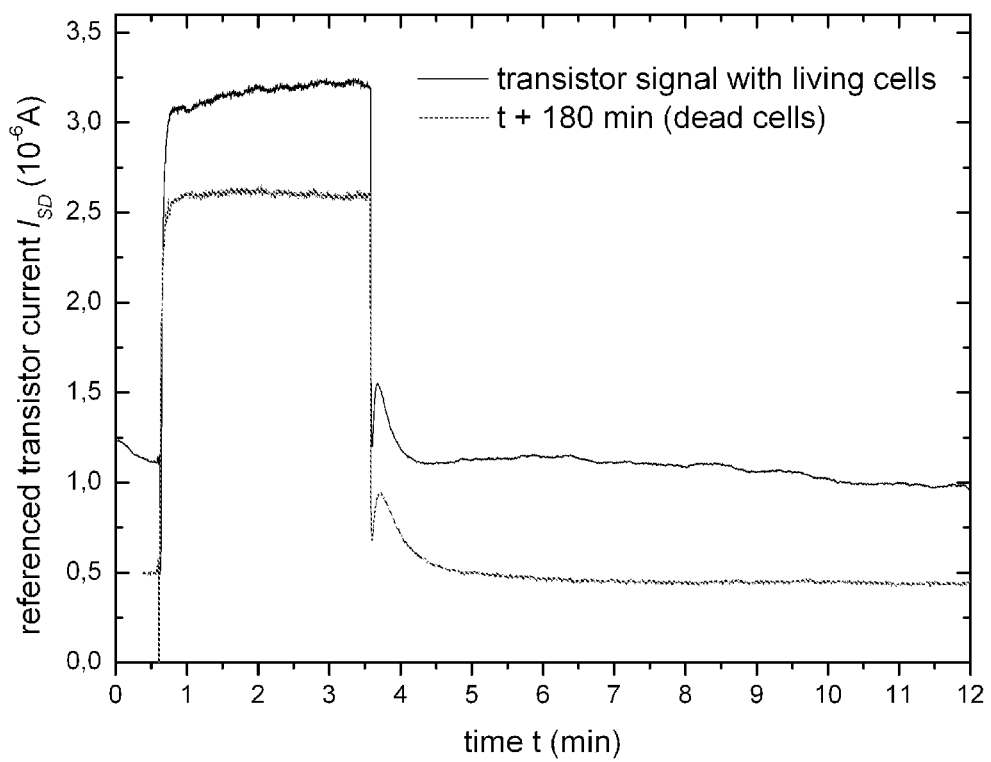

FIG. 4: Referenced transistor signals. Cells were grown on one of the chips. The signal of the living cell irradiation shows an increase (5.1 mGy/s, 3 min) during the exposure to X-rays. The red curve shows the irradiation of the same sample repeated after t+180 min. As the cells now have lost their vitality, biological reactions are no longer expected and the curve shows a flat progression, comparable to the reference curve without cells in FIG. 3.

Figure 5:
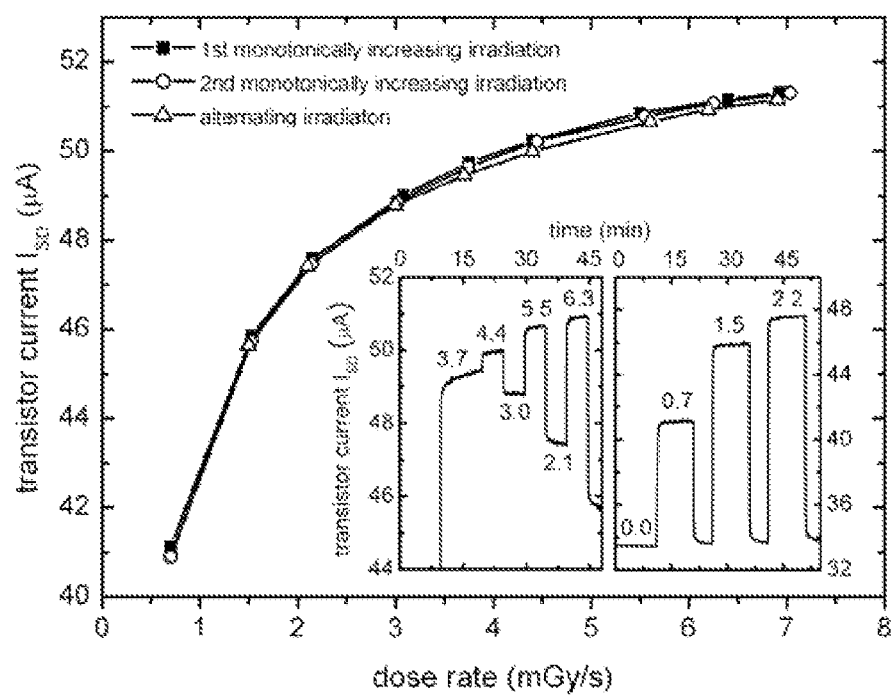

FIG. 5: Source-drain current of an AlGaN/GaN HEMT as a function of dose-rate (X-rays, 150 kV). The insets show the measurement of the absolute source-drain current as a function of time under pulsed X-ray irradiation with various dose-rates of both alternating (left inset) and intermittent (right inset) intensity. The numbers in the insets give the dose rates in mGy/s. The complete experiment, including two irradiation series, was performed twice.

Figure 6:
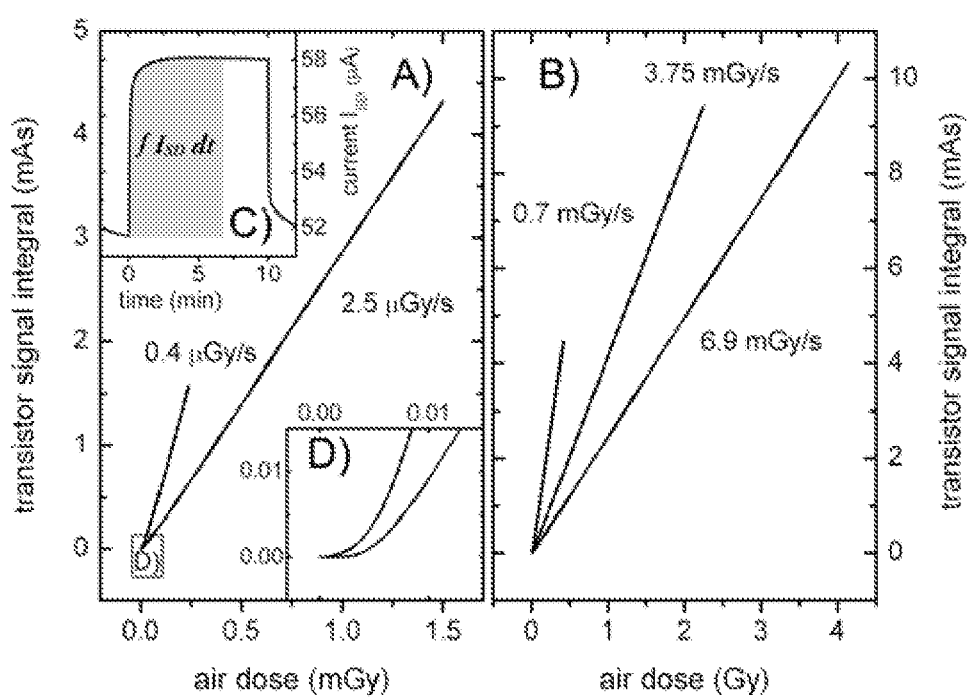

FIG. 6: (A,B) Time integral of the transistor signal shows a linear correlation with the total dose in air. A typical response signal for a dose rate of 1.6 μGy/s is given in inset (C). The inset (D) shows an in-going drift of the signal at the beginning of the pulse, but linear behavior is observed down to ~10 μGy. The measurements in the low dose range were performed with 18 kV X-rays and the high dose measurements with 150 kV X-rays. Transistors were irradiated for 10 min at different dose rates.

Figure 7:
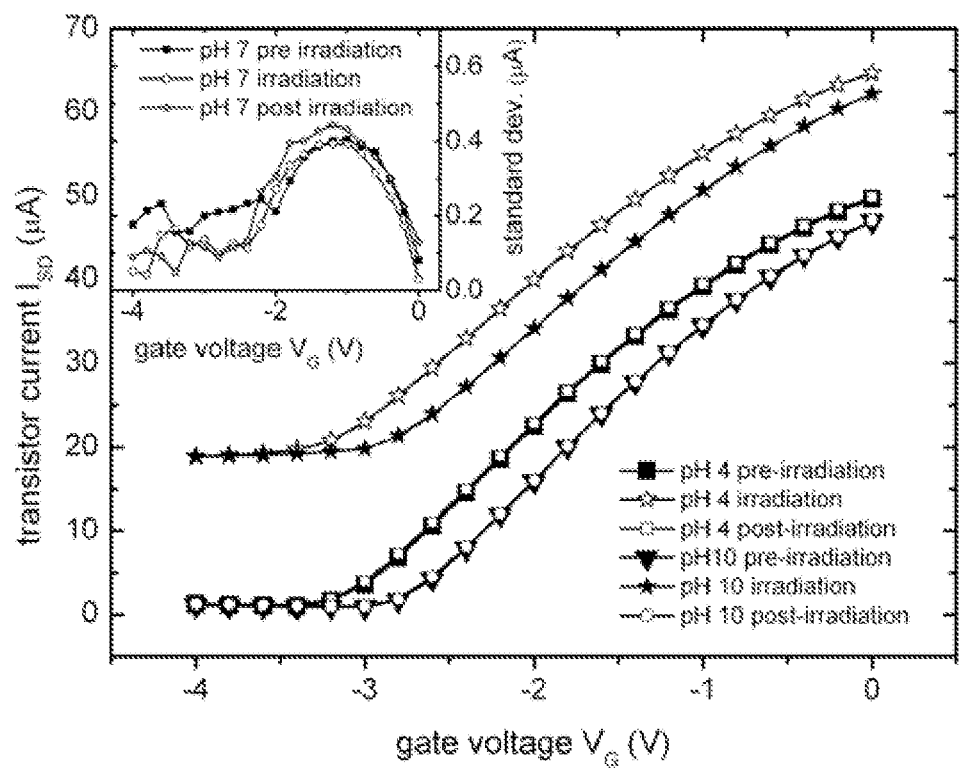

FIG. 7: Characteristic curves of a GaN-device in solution before, during, and after irradiation with a dose-rate of 2.9 mGy/s at pH 4 and pH 10. To achieve equilibrium, VG was first cycled between 0 V and −4 V five times. The plotted data were then obtained by averaging of five consecutive cycles per data series. The inlay shows the standard deviation of the characteristic curves at pH 7 as a function of gate potential which gives a measure of the device hysteresis.

Figure 8:
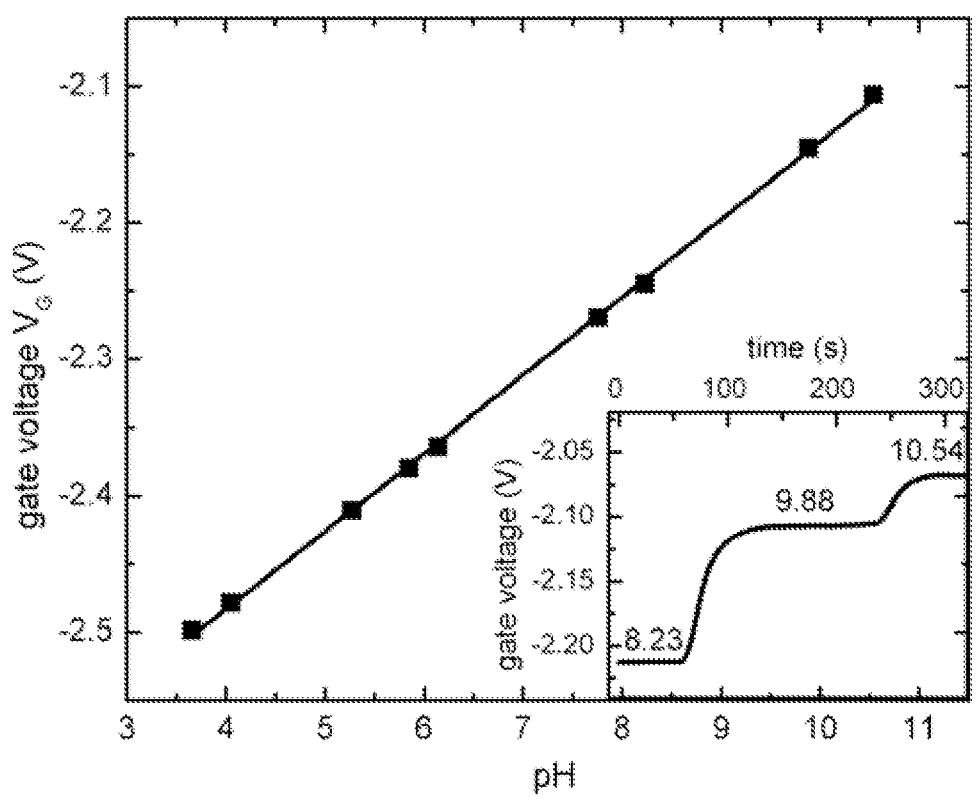

FIG. 8: Titration during a continuous irradiation with a dose-rate of 1.4 mGy/s. The slope of the linear pH response yields a transistor sensitivity of 57 mV/pH. The inset illustrates a section of the measured gate voltage VG at different titrated pH-values. Continuous irradiation was performed with 150 kV X-rays.

FIG. 9: Cross-section of an exemplary HEMT transistor

The Examples Also Illustrate the Present Invention:

Example 1: Monitoring of Stimulated Cell Responses on AlGaN/GaN-Nanostructures

Cell communication pathways lead to a transfer of primary and secondary messengers across the cellular membrane. The decoding of these pathways is the key to understand sophisticated cell homeostasis. Here, we present a measurement approach based on semiconductor nanostructures, being capable of recording cell potential responses, caused by charged extra cellular messengers, during irradiation experiments in long-term measurements. AlGaN/GaN heterostructures provide electron- and ion-sensitive transistor gate layers. The electrical properties and therefore the conductivity of the system highly depend on the chip surface potential, which is changed by ion fluxes across cell membranes. This enables specific investigations for cell responses and their chronological sequence. Although the devices are sensitive to radiation, the heterostructures are operable with a stable and repeatable behavior during exposure to X-rays. We measured transistor signal changes up to 0.13 μA within 60 s caused by irradiated cells. The possibility of measuring cell potentials, not only after irradiation experiments but also during the irradiation itself expands the examination restrictions considerably.

The intercellular exchange of biological signals, followed by an intracellular biochemical communication, is an integral part of cell proliferation.[1] Microelectrode arrays[2-4] and field effect transistors (FET's)[5] are used for the recording of these electrical cell signals. The development of high electron mobility transistors (HEMT's) formed by AlGaN/GaN-nanostructures provides a highly sensitive possibility for non-invasive extra cellular monitoring of cell activities.[6] Here, we report the utilization of such semiconductor devices as a biosensor for long-term investigations. We demonstrate the biocompatibility of the device surfaces and the recording of X-ray stimulated electrical signals from fibroblasts by combining semiconductor measurement techniques with irradiation experiments. In order to use $Ca^{2+}$ as a messenger, biological cells overcome the homeostatic control by employing sophisticated short burst $Ca^{2+}$ release mechanisms by using either $InsP_3$ or ryanodine receptors.[7] We developed an experimental set-up to detect very small electrical signals produced by living cells during and after irradiation experiments. Long-term measurements became possible by a simultaneous irradiation of two GaN-transistors and, thus, a compensation of any direct X-ray related spurious signals and temperature drifts. Group III-nitrides are chemically stable under physiological conditions, non-toxic to living cells[8] and withstand high X-ray radiation doses. To exclude any radiation induced intrinsic effects, we carefully characterized the response of the AlGaN/GaN-heterostructures to X-ray radiation. The nanostructures show a stable and repeatable operation during irradiation conditions. Furthermore, the biocompatibility of the transistor surfaces was ensured by both, DNA repair and cell growth studies (FIG. 1). Results are comparable to previous published data.[9] Fabrication and physical properties of the HEMT devices are described in G. Steinhoff et al.[10]

[1] Hereditary Effects of Radiation, UNSCEAR Report 2001
[2] C. A. Thomas Jr., P. A. Springer, G. E. Loeb, Y. Berwald-Netter, and L. M. Okun, Exper. Cell Res. 74, 61-66 (1972)
[3] P. Connolly, P. Clark, A. S. G. Curtis, J. A. T. Dow, and C. D. W. Wilkinson, Biosens. Bioelectron. 5, 223-234 (1990)
[4] F. Heer, W. Franks, A. Blau, S. Taschini, C. Ziegler, A. Hierlemann, and H. Baltes, Biosens. Bioelectron. 20, 358-366 (2004)
[5] P. Bergveld, J. Wiersma, and H. Meertens, IEEE Trans. Biomed. Eng. 23, 136-144 (1976)
[6] G. Steinhoff, B. Baur, G. Wrobel, S. Ingebrandt, A. Offenhausser, A. Dadgar, A. Krost, M. Stutzmann, and M. Eickhoff, Appl. Phys. Lett. 86, 033901 (2005)
[7] M. J. Berridge, Journ. Exper. Biol. 200, 315-319 (1997)
[8] G. Steinhoff, O. Purrucker, M. Tanaka, M. Stutzmann, and M. Eickhoff, Adv. Funct. Mater. 13, 841-846 (2003)
[9] K. Rothkamm, M. Löbrich, PNAS, Vol. 100, No. 9, 5057-5062 (2003)
[10] G. Steinhoff, M. Hermann, W. J. Schaff, L. F. Eastman, M. Stutzmann, and M. Eickhoff, Appl. Phys. Lett. 83, 177-179 (2003)

The transistors were electrically operated with floating gate and a constant source-drain bias of 120 mV. Before wiring and passivation, the chips were cleaned with acetone and iso-propanol in an ultrasound bath. Before every measurement, the surfaces were cleaned with 70% ethanol and sterilized for 30 minutes under UVC-light. Subsequently, they were coated with fibronectin solution (12.5 µl fibronectin in 1 ml Hank's balanced salt solution) at 37° C. for 30 minutes. For our cell experiments, mouse connective fibroblasts L-929 were cultivated in RPMI 1640 Medium (w 5.5 g/l Phenol red, w 2.0 g/l NaHCO$_3$, w 25 mM HEPES, w stable glutamine) with 10% fetal bovine serum (FBS) and 1% penicillin/streptomycin (10000 units/ml penicillin, 10 mg/ml streptomycin) at 37° C. and 95% humidity. Cells were grown to a confluent layer. Irradiation experiments were performed with a medical X-ray machine Stabilipan TR300f (Siemens AG, 80333 München, Germany).

A linear relationship between the pH-value at the transistor gate and the source-drain current was demonstrated in a previous publication.[9] The devices had a pH dependence, which was confirmed by a titration from 5.6-8.4 pH and showed a −0.32 µA/pH sensitivity in the region of interest. The pH of the HCl and NaOH solutions was determined with a pH-meter, type CyberScan 500 (Eutech Instruments Europe, Nijkerk, Netherlands). To evaluate any possible X-ray related spurious transistor responses, we irradiated one bare chip with different dose rates between 1 and 12 mGy/s. Every exposure to radiation was repeated once with the same settings to analyze the reproducibility. The transistor was irradiated for one minute each time with different doses with a break of 4 min between the irradiations. In this time the transistor signal declines. Furthermore, the chip was exposed several times with the same dose rate but under different irradiation times to examine their influence. The time between the different irradiations was also 4 min. A radiation dependent change of the source-drain current ΔI is observable up to high dose rates. (FIG. 2). Cell irradiation experiments were typically performed with dose rates of 4-7mGy/s. Thereby the transistors are operated in an active regime. To demonstrate the reproducibility of the X-ray dependence, we repeated each measurement under nominally identical conditions (green symbols and line). The measured current increase clearly depends on the dose rate and also on the irradiation time (not shown). As our transistors show a stable and reproducible performance during irradiation experiments, we could compensate for the direct radiation response, by simultaneously irradiating two identical transistors, one of which contained the cells and the other one served as a reference.

Then, the signal from the second reference transistor is subtracted from the measurement signal of the other. The result is the sensor response $I_{SD}$. Because both transistors, due to the manufacturing, wiring and passivation processes, turned out not to be completely identical, the referenced curve is not completely independent of external physical parameters (temperature, pH and irradiation) but our reference method still reduces the effects considerably.

The most striking effect of cell irradiation is seen in FIG. 3 (dose rate 7.1 mGy/s). In the lower trace (black curve), we depict the reference response $I_{SD}$ (no cells but buffer solution present) as a function of time. The same quantity is plotted for the case that living cells were present on one of the sensor areas (red curve). Clearly, we see a decrease of the signal as compared to the reference curve. We show the same experiment, this time, however, for the case where the living cells were interchanged between the two sensor areas (green curve). The green curve exhibits a slight increase during irradiation, whereas the red curve decreases with the approximately same gradient. We see that the major sensor response during irradiation is due to the photo effect as described above. Nevertheless, we feel safe to state that irradiation of living cells leads to a small but detectable sensor response. Signal changes caused by the cells are 0.13 µA compared to the reference curve.

Comparing a referenced irradiation of living cells with cells that lost their vitality further supports this assumption. It is possible to differentiate between a demanded signal generation by cell responses and a physical signal generation, e.g. a simple interaction of X-rays with the biological material. FIG. 4 shows a signal increase $I_{SD}$ during irradiation of vital cells (black curve) as in the previous experiment but with a dose rate of 5.1 mGy/s. After three hours at room temperature the cells have lost their vitality and the sensor response is flat again, just like for the reference measurement without cells. (FIG. 4, red curve). This clearly indicates a biological signal generation by living cells.

In conclusion, the semiconductor nanostructures can be used as biosensors, which allow long-term measurements of stimulated cell responses. The system shows a stable and reproducible sensor response under X-ray radiation and is sensitive enough to detect extra cellular messengers. This can give new insights in radiation biology, for example signaling pathways, $Ca^{2+}$ burst measurements or cell-cell communication analysis.

Example 2: Real-Time X-Ray Response of Bio-Compatible Solution Gate AlGaN/GaN-HEMT Devices We present the real-time X-ray irradiation response of charge and pH sensitive solution gate AlGaN/GaN high electron mobility transistors. The devices show stable and reproducible behavior under and following X-ray radiation, including a linear integrated response with dose into the µGy range. Titration measurements of devices in solution reveal that the linear pH response and sensitivity are not only retained under X-ray irradiation, but an irradiation response could also be measured. Since the devices are biocompatible, and can be simultaneously operated in aggressive fluids and under hard radiation, they are well-suited for both, medical radiation dosimetry and bio-sensing applications. The capability for in situ monitoring of biological systems is critically important to the modern medical community. One aspect of this research is the development of methods to study the real-time effect of radiation on cells prior to, during, and after exposure. In recent years, wide-bandgap semiconductors have made an entrance into this research field, and GaN has shown particularly promising characteristics: AlGaN/GaN high electron mobility transistors (HEMTs) are reported to be biocompatible.1,2 With an additional GaN capping layer, the devices are operable in aqueous solutions, are to a large degree chemically inert, and show a highly linear pH sensitivity.3 Furthermore, these devices have been used for the detection of gases, polar fluids, specific ions, and cell responses.1-4 Here, we expand the application range of GaN devices by demonstration of simultaneous solution phase pH measurements and radiation detection using ion sensitive field effect transistors (ISFETs) based on AlGaN/GaN HEMTs. The devices show a stable, repeatable, and sensitive response to X-ray radiation and retain their pH sensitivity during irradiation. Due to their small size and their operability in wet environments, such devices are well suited for in vivo dosimetry and they provide a means for simultaneous measurement of biochemical and radiation responses in harsh environments. The HEMT devices used for this study were produced using a commercial MOCVDbased growth process by Top GaN (Warsaw, Poland) with a 2.6 nm GaN capping layer. The fabrication method and physical properties of the HEMT devices are described in previous publications.5,6 The measurement set-up consisted of a single electrochemical cell with: a standard glass-electrode (pH/Ion-Meter Metrohm 781), a Pt-counter electrode, a Ag/AgCl reference electrode, and the ISFET configured as the working electrode. The active area of the transistor (0.88 mm2) was irradiated, during operation, by a medical X-ray system (Stabilipan TR300f, Siemens AG) with a 4 mm Al filter and reference measurements of doses in air were recorded with a dose area product meter (Diamentor M4, PTW). For low dose experiments a cabinet X-ray system (MX-20, Faxitron X-ray LLC) was utilized. The solution measurements were performed in 10 mM HEPES buffer and 0.1 M NaCl or KCl, titrated with NaOH or KOH, and HCl diluted with buffer. All experiments were performed in a completely darkened environment due to the light sensitivity of the transistors. In order to confirm the stability and reproducibility of device performance under and following X-ray irradiation, multiple series of dose-rate dependant transport measurements were performed. FIG. 5 shows the results of a 150 kV pulsed X-ray irradiation series, with the change of the source-drain current, ISD, at a fixed potential of 120 mV and a floating gate potential plotted versus the dose-rate. As shown in the inlay of FIG. 5, irradiation was performed with pulses of 10 min duration at 15 min intervals. A monotonic increase of the source-drain current with X-ray dose-rate due to generation of photo-excited carriers is observed. Comparison of results from a repetition of the dose series yields excellent reproducibility without any noticeable permanent performance alteration after a total dose of 60 Gy. These small deviations demonstrate that the devices are well-suited for dosimetry applications and they provide an internal calibration for the absolute received dose-rate under solution operation. We note that measurements of the source-drain current response in solution conditions showed similar reproducibility without any special surface treatment of the device.

While the magnitude of the transistor response correlates with the dose rate, the accumulated transistor signal is expected to be proportional to the total absorbed dose. FIG. 6 shows the integrated transistor response in air. We observe a highly linear relationship for different dose rates, even into the very low dose range (to ~10 µGy). In comparison, MOSFET-based radiation detectors, which have become essential tools in radiology,7-10 reach their detection limits in the low mGy region.7,8 The GaN-devices expand this limit down into the µGy-regime, as shown in FIGS. 6(A & D).

In addition to the characterization of X-ray response under dry conditions, we show that the transistors retain their sensitivity to potential changes at the GaN surface during irradiation in solution. FIG. 7 shows the source-drain current as a function of the gate potential, VG, for a constant source-drain voltage, VSD, of 120 mV. The transistor was characterized at pH 4, pH 7, and pH 10, before, during, and after X-ray irradiation with a dose-rate of 2.9 mGy/s at 150 kV. Owing primarily to photo-generation of electron-hole pairs in the GaN buffer and capping layers, each complete characteristic curve is offset to higher currents during irradiation. This radiation dependent offset could be used under negative gate biasing, below −3.5 V, to make an independent dosimetry measurement. In FIG. 7 we have plotted averaged values from cyclic measurements for the gate voltage VG since the source-drain current shows hysteresis. The standard deviation of the averaged cycles, shown in the inset of FIG. 7, gives the magnitude of hysteresis as a function of the gate potential and shows very little difference between the non-irradiated and irradiated device. The pH dependence, which can be explained with the site binding model,11-13 is similar in both the non-irradiated and irradiated cases.

In order to ascertain whether a radiated device would linearly respond to pH in a similar manner to the non-radiated devices reported by Steinhoff et al., 3 a transistor was continuously irradiated in an aqueous solution while the pH was varied by titration. To gain the surface charge difference per pH, the source-drain current, ISD, was kept constant by adjusting the gate potential with a constant source-drain voltage of 120 mV. The regulated changes of VG are plotted as a function of the pH electrode reading in FIG. 8. The slope, corresponding to a pH-sensitivity of 57 mV/pH, was extracted by linear regression following subtraction of the in-going drift. This value is comparable to the sensitivity without radiation of 56 mV/pH,3 and differs as a consequence of a slightly elevated operational temperature since our experiments were performed at room temperature and those of Ref. 3 were controlled to 20° C. We note that the dose-rate of 1.4 mGy/s inside the electrolyte solution was determined using the internal self-calibration curve of the GaN-device signal response in air shown in FIG. 5.

In conclusion, we find that GaN HEMT devices, configured as ISFETs operating in electrolytes, retain their pH sensitivity during X-ray irradiation in a stable and reproducible manner. Moreover, our findings suggest that the fundamental device characteristics could be utilized for separating the irradiation signal from the pH response without compromising the operational stability of the device. The reproducible enhancement of the source-drain current with X-ray dose rate further provides an internal calibration for the received photon flux under aqueous solutions and establishes that such devices are well suited for combined hard radiation and ion-sensitive measurements in a range of harsh environments. They are thus ideally suited for future integrated radiation dosimetry and bio-sensing medical applications 1. G. Steinhoff, O. Purrucker, M. Tanaka, M. Stutzmann, and M. Eickhoff, Adv. Funct. Mater. 13, 841 (2003).
2. G. Steinhoff, B. Baur, G. Wrobel, S. Ingebrandt, A. Offenhäusser, A. Dadgar, A. Krost, M. Stutzmann, and M. Eickhoff, Appl. Phys. Lett. 86, 033901 (2005).
3. G. Steinhoff, M. Hermann, W. J. Schaff, L. F. Eastman, M. Stutzmann, and M. Eickhoff, Appl. Phys. Lett. 83, 177 (2003).
4. M. Eickhoff, J. Schalwig, G. Steinhoff, O. Weidemann, L. Görgens, R. Neuberger, M. Hermann, B. Baur, G. Müller, O. Ambacher, and M. Stutzmann, phys. stat. sol. (c) 6, 1908 (2003).
5. R. Dimitrov, M. Murphy, J. Smart, W. Schaff, J. R. Shealy, L. F. Eastman, O. Ambacher, and M. Stutzmann, J. Appl. Phys. 87, 3375 (2000).
6. M. J. Murphy, K. Chu, H. Wu, W. Yeo, W. J. Schaff, O. Ambacher, L. F. Eastman, T. J. Eustis, J. Silcox, R. Dimitrov, and M. Stutzmann, Appl. Phys. Lett. 75, 3653 (1999).
7. T. T. Yoshizumi, P. C. Goodman, D. P. Frush, G. Nguyen, G. Toncheva, M. Sarder and L. Barnes, American Journal of Roentgenology 188, 1332 (2007)
8. D. J. Peet and M. D. Pryor, The British Journal of Radiology 72, 562 (1999)
9. D. J. Brenner, Med. Phys. 32, 3225 (2005)
10. C. F. Chuang, L. J. Verhey, and P. Xia, Med. Phys. 29, 1109 (2002)
11. D. E. Yates, S. Levine, and T. W. Healy, J. Chem. Soc., Faraday Trans. 170, 1807 (1974).
12. L. Bousse, N. F. De Rooij, and P. Bergveld, IEEE Trans. Electron Devices ED-30, 1263 (1983).
13. C. D. Fung, P. W. Cheung, and W. H. Ko, IEEE Trans. Electron Devices ED-33, 8 (1986).

The invention claimed is:

1. A method for monitoring a cell signal produced by living cells in response to external stimulation, comprising:
   (a) providing a device for monitoring a cell signal produced by living cells in response to external stimulation comprising, said device comprising
      (i) at least one discrete area comprising a high electron mobility transistor (HEMT);
      (ii) cells attached to a gate surface of said HEMT, the cells characterized as not being able to spontaneously generate an electrical signal; and
      (iii) at least a second discrete area comprising a second HEMT, said second area being free of cells; and
   (b) monitoring a cell signal produced by living cells in response to external stimulation, said monitoring comprising measuring surface potential (pH) of the cells simultaneously with measuring (i) radiation dosimetry, (ii) radiation dose rate, or both (i) and (ii).

2. The method of claim 1 where step (b) comprises monitoring the cell signal in real time.

3. The method of claim 1 where, in step (a) the cells attached to the gate surface of said HEMT are exposed to ionizing radiation which provides the external stimulation.

4. The method of claim 1 where step (b) comprises measuring surface potential (pH) of the cells simultaneously with measuring (i) radiation dosimetry.

5. The method of claim 1 where, in step (a) the cells attached to the gate surface of said HEMT are exposed to a test compound which provides the external stimulation.

6. The device of claim 1 wherein the second discrete area is free of a biomolecular coating.

7. The method of claim 1, wherein said HEMT is a AlGaN/GaN-hetero-structure.

8. A method for monitoring a cell signal produced by living cells in response to external stimulation, comprising:
   (a) providing at least one discrete area comprising a HEMT;
   (b) growing/attaching cells onto a gate surface of said HEMT, the cells characterized as not being able to spontaneously generate an electrical signal;
   (c) providing at least a second discrete area comprising a second HEMT being free of cells; and
   (d) monitoring a cell signal produced by living cells in response to external stimulation, said monitoring comprising measuring changes of surface potential (pH) of the cells simultaneously with measuring (i) radiation dosimetry, (ii) radiation dose rate, or both (i) and (ii).

9. The method of claim 8 where step (d) comprises monitoring the cell signal in real time.

10. The method of claim 8 where, in step (b) the cells are exposed to ionizing radiation which provides the external stimulation.

11. The method of claim 8 where step (d) comprises measuring changes of surface potential (pH) of the cells simultaneously with measuring, (ii) radiation dose rate.

12. The method of claim 8 where, in step (b) the cells are exposed to a test compound which provides the external stimulation.

* * * * *